(12) United States Patent
Adams

(10) Patent No.: US 8,620,045 B2
(45) Date of Patent: Dec. 31, 2013

(54) SYSTEM, METHOD AND ARTICLE FOR MEASURING AND REPORTING CRANIOMANDIBULAR BIOMECHANICAL FUNCTIONS

(76) Inventor: Bruce William Adams, West Vancouver (CA)

( * ) Notice: Subject to any disclaimer, the term of this patent is extended or adjusted under 35 U.S.C. 154(b) by 98 days.

(21) Appl. No.: 13/273,178

(22) Filed: Oct. 13, 2011

(65) Prior Publication Data

US 2012/0107763 A1 May 3, 2012

Related U.S. Application Data

(60) Provisional application No. 61/393,419, filed on Oct. 15, 2010.

(51) Int. Cl.
*G06K 9/00* (2006.01)
*A61C 1/00* (2006.01)
*A61C 5/00* (2006.01)

(52) U.S. Cl.
USPC .............................. 382/128; 433/29; 433/215

(58) Field of Classification Search
USPC ......... 382/128, 129, 130, 131, 132, 133, 134; 433/29, 68, 69, 79, 140, 173, 215, 433/201.1; 378/4, 8, 21–27, 101; 128/915, 128/916, 920, 922
See application file for complete search history.

(56) References Cited

U.S. PATENT DOCUMENTS

| 4,837,732 | A * | 6/1989 | Brandestini et al. ............ 433/29 |
| 7,664,298 | B2 * | 2/2010 | Lang et al. .................... 382/128 |
| 7,758,345 | B1 * | 7/2010 | Christensen .................. 433/214 |
| 8,435,033 | B2 * | 5/2013 | Gross et al. ..................... 433/75 |
| 2009/0253095 | A1 * | 10/2009 | Salcedo et al. .................. 433/75 |

* cited by examiner

*Primary Examiner* — Abolfazl Tabatabai

(57) ABSTRACT

The present invention provides a motion analysis system for measuring the relative function of one anatomical structure to another based on optical fiducial markers tracked in a series of images and in turn data, where the components of hard and soft tissue are used in analysis and where the image data can be compared in a time series such that probabilities of involvement with various tissues can be correlated to the image data.

The system measures displacement at various positions and can relate the data to various muscle and other soft tissue variations within the constraints of the anatomy and physiology including motion in three dimensional space, including rotations and translations and functions including velocity and acceleration.

41 Claims, 18 Drawing Sheets

A                    B

Sagittal (A.) and frontal (B.) views of Maxillary and Mandibular optical targets on a harness Fig 1. Plots of x axis accelerometer data, optical data and integrated data to show displacement over time.

FIGURE 2
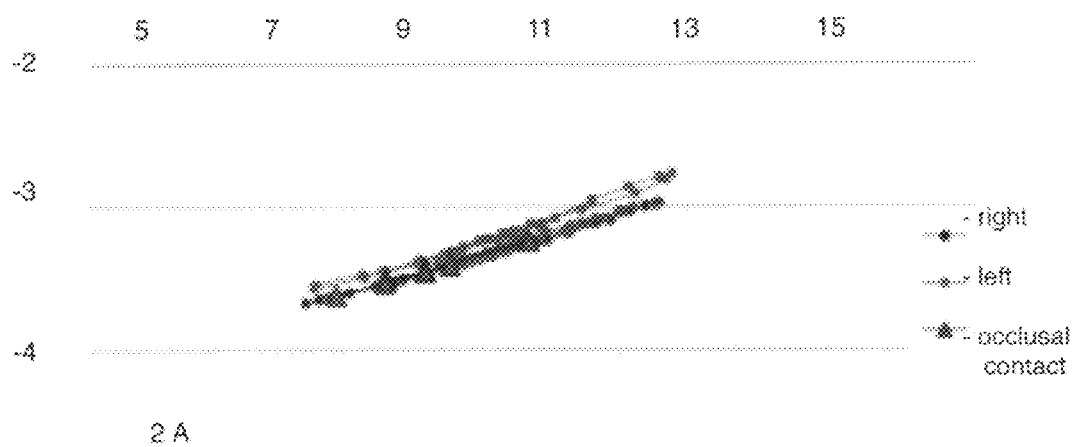
2A
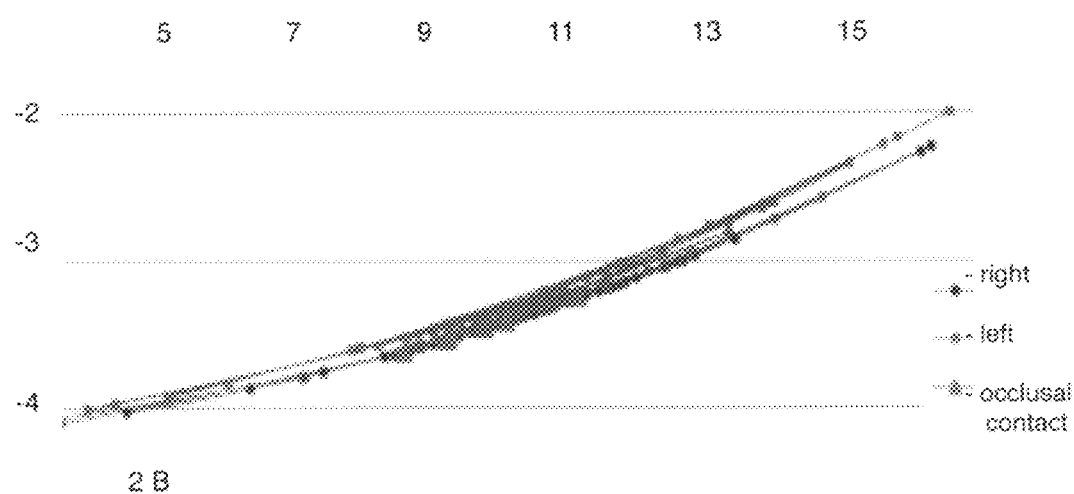
2B
Fig 2 Plots of displacement data of the contact point of the condyle with the disk in the glenoid fossa showing normalized data that integrates optical data, (A) vs accelerometer only data (B)

Fig 3 Incisal guidance and free translation without contact. The average direction of mandibular forces is shown orthogonally to the translations.

Fig 4. Translation during movement from the retruded position to CO are compared and can be related to both dental and Temporomandibular joint guidance.

Fig 5. opening with muscle retrusion involvement as compared to closing from optical data Fig 6. Ideal curve of spee based on Temporomandibular joint guidance from optical data with curve of dentition in sagittal view Fig 7. Right side translations. Right buccal cusps require superior and retruded position of Temporomandibular joint and masseter involvement. from optical data Fig. 8 CO is in Gelb 4 / 7 position the original TM locus, and showing translation from there.

Fig 9. Normalized Data from two different images shows how mandibular tracking points can be extracted and measured from their normalized relative maxillary reference position.

Fig 10 Saggital (A.) and Frontal (B.) views of Maxillary and Mandibular optical target on a harness Fig 11 Clinical Coordinate System Fig 13 Diagnostic Flow chart

FIGURE 14

| protocol | CR - CO | | | | | |
|---|---|---|---|---|---|---|
| 2 | data / suggests some resistance and rotation | | | | | |
| | action | | | | | |
| | rotation | | | translation | | |
| muscles | α | γ | β | x | y | z |
| masseter | | | | 2 | | |
| temporalis | | | | -1 | | |
| lateral pterygoid | | | | 2 | | |
| medial pterygoid | | 1 | | | 1 | |
| digastric | | | | | | |
| hyoid | | | | | | |

Fig 14 Muscles versus forces table

Fig 15 Incorporation of other sensors including accelerometer data or other data with optical data Fig 16 Sample collection Architecture Fig 17 Clinical process and documentation collection Architecture

SYSTEM, METHOD AND ARTICLE FOR MEASURING AND REPORTING CRANIOMANDIBULAR BIOMECHANICAL FUNCTIONS

CROSS-REFERENCE TO RELATED APPLICATIONS

This application claims benefit under 35 U.S.C. 119(e) to U.S. provisional patent application Ser. No. 61/393,419, filed Oct. 14, 2010, which is incorporated herein by reference in its entirety.

FIELD OF THE INVENTION

The present invention pertains to the field of Dentistry and in particular to measurement of temporomandibular joint and occlusal relationships.

BACKGROUND

The practice of restorative dentistry and treatment of the associated structures of the dentition and jaws has evolved such that the analysis of the temporomandibular joints is generally not a part of routine dentistry. The issues surrounding centric occlusion, centric relation or the position of maximum intercuspation, are typically managed intuitively by dental practitioners.

Physical registrations at various positions of occlusion are sometimes used to provide additional information about the interocclusal relationships, especially when the practitioner is undertaking prosthodontic and restorative procedures. These are typically made by having the patient close their jaws together on some type of registration material such as wax or polysiloxane. Dental casts are typically mounted with this registration on an articulator and used to simulate the static relationship of the jaw in occlusion. The registration of centric occlusion is often used to describe the position at which the teeth come together and used in context with treatment to the dentition, especially the position of maximum intercuspation, however these measurements typically do not allow for routine analysis of the temporomandibular joints.

In practice, occlusal aspects of restorations may be fitted by trial and error on the model and adjusted in size and shape as needed until a satisfactory size and shape are attained. Mechanical articulators include an upper member and a lower member that are connected together by a pair of pivotal couplings (such as ball and socket joints). The model of the upper arch is connected to the upper member of the articulator, while the model of the lower arch is connected to the lower member of the articulator. In general, the couplings enable the two models to move toward and away from each other but cannot accurately mimic the certain movements of the patient's jaws.

As can be appreciated, however, the technique of articulation that is described above is time consuming and must be carefully executed to ensure that the resulting articulation properly records a useful relationship of the patient's occlusion.

Therefore there is a need for improved methods for measuring maxillo mandibular relationships and relating this information to a treatment plan.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a system and method for measuring and reporting the low frequency relative functions of dental anatomical structures. In accordance with an aspect of the present invention, there is provided a motion analysis system for measuring the absolute changes and relative function of one anatomical structure to another based on three dimensional optical target tracking.

In accordance with another aspect of the present invention, the low frequency data, can be combined with high frequency including data from other measurement sources and/or also including data from computer models, to create a mathematical representation of the cranio-mandibular relationships.

BRIEF DESCRIPTION OF THE FIGURES

FIG. 2 illustrates plots of displacement data of the contact point of the condyle with the disk in the glenoid fossa. The data has been filtered to compensate for the rotations. High frequency data is still obvious in the accelerometer only data. The low frequency filter and integration with optical data is used to spatially normalize it.

An axial (also known as transverse or horizontal) plane is an X-Y plane, parallel to the ground, which separates the superior from the inferior.

A coronal (also known as frontal) plane is a Y-Z plane, perpendicular to the ground, which separates the anterior from the posterior.

A sagittal (also known as lateral) plane is an X-Z plane, perpendicular to the ground, which separates left from right. The midsagittal plane is the specific sagittal plane that is exactly in the middle of the body.

Figure 12:
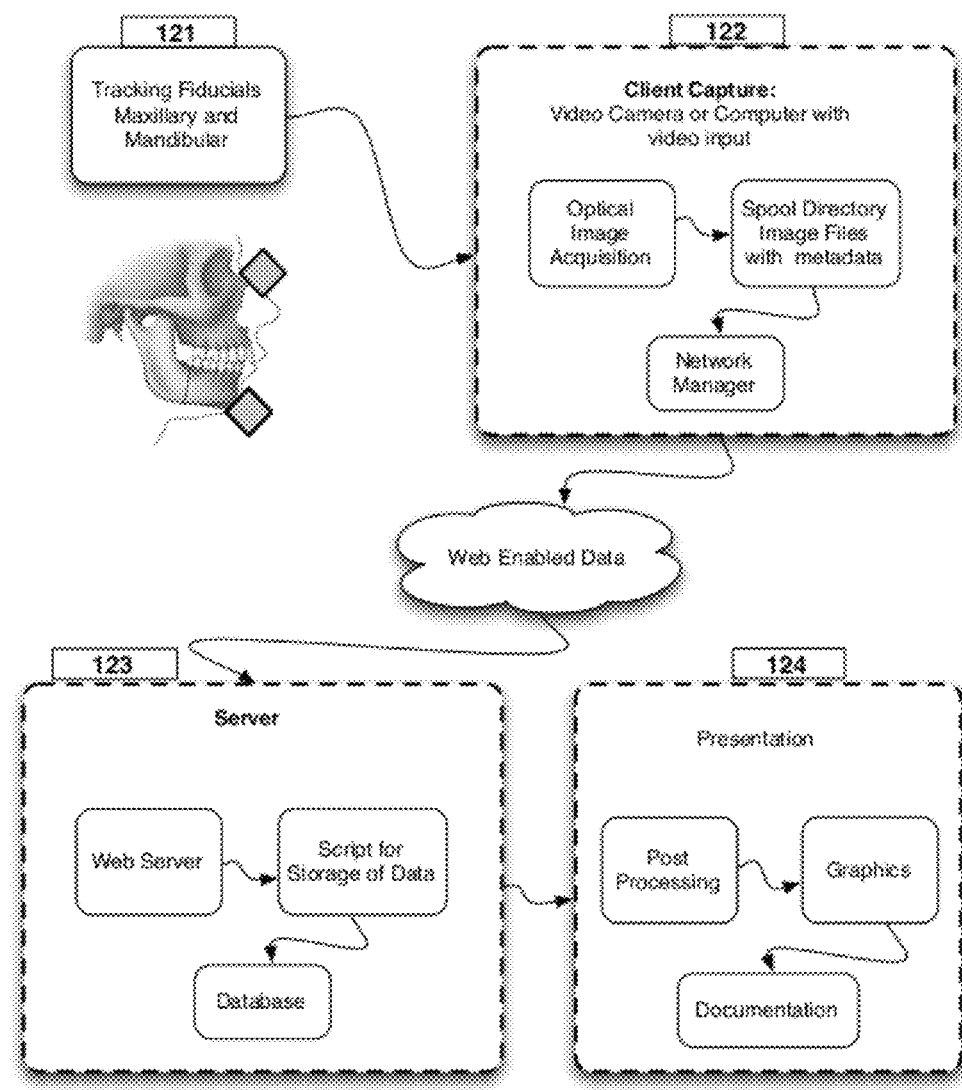

FIG. 12 illustrates the high level system architecture.

Figure 13:
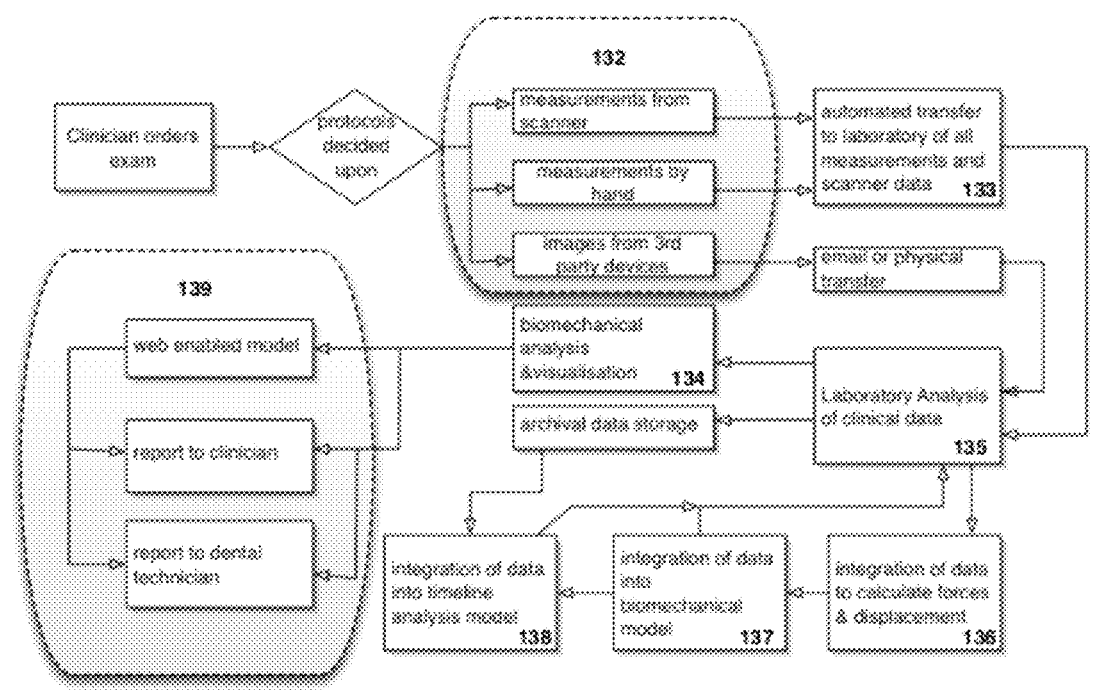

FIG. 13 illustrates the movement and analysis of data including protocol decisions, data transfer and integration of data into physical, biomechanical and timeline analysis and the reporting and visualisation process.

FIG. 14 illustrates muscle activity during protrusion from Centric Relation to Centric Occlusion (CR to CO) where temporomandibular joint rotation is out of pattern with normal.

Figure 15:
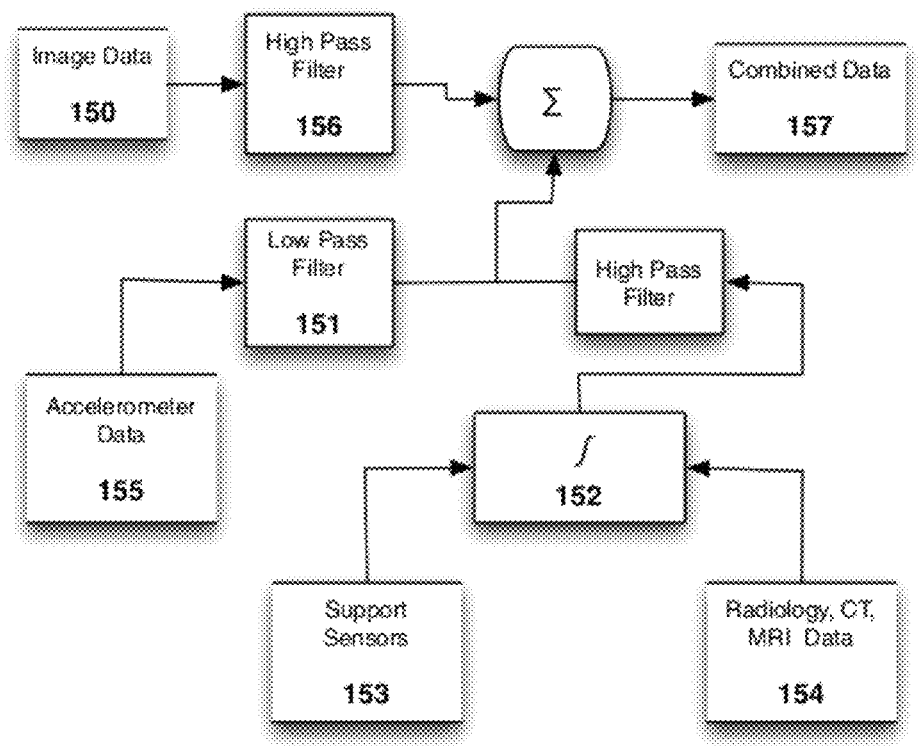

FIG. 15 illustrates the method used to integrate data from sensors and other imaging sources including accelerometer data or other from sensors such as a gyroscope or radiographic images with the optical data.

Figure 16:
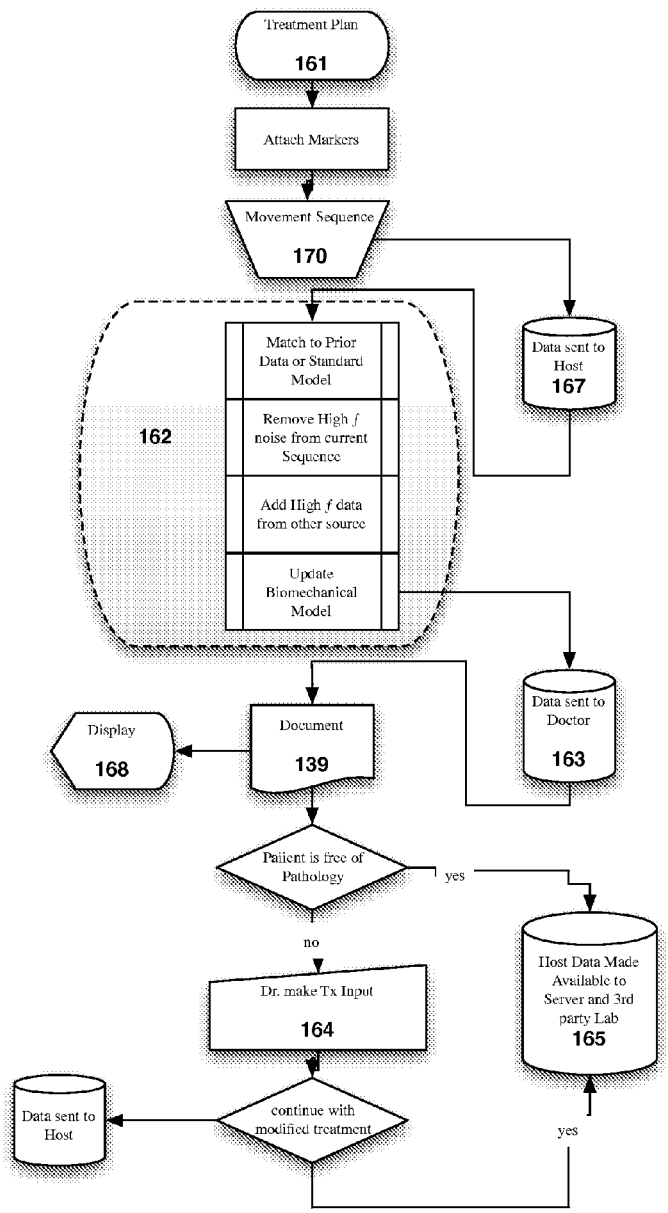

FIG. 16 illustrates the sample collection architecture.

Figure 17:
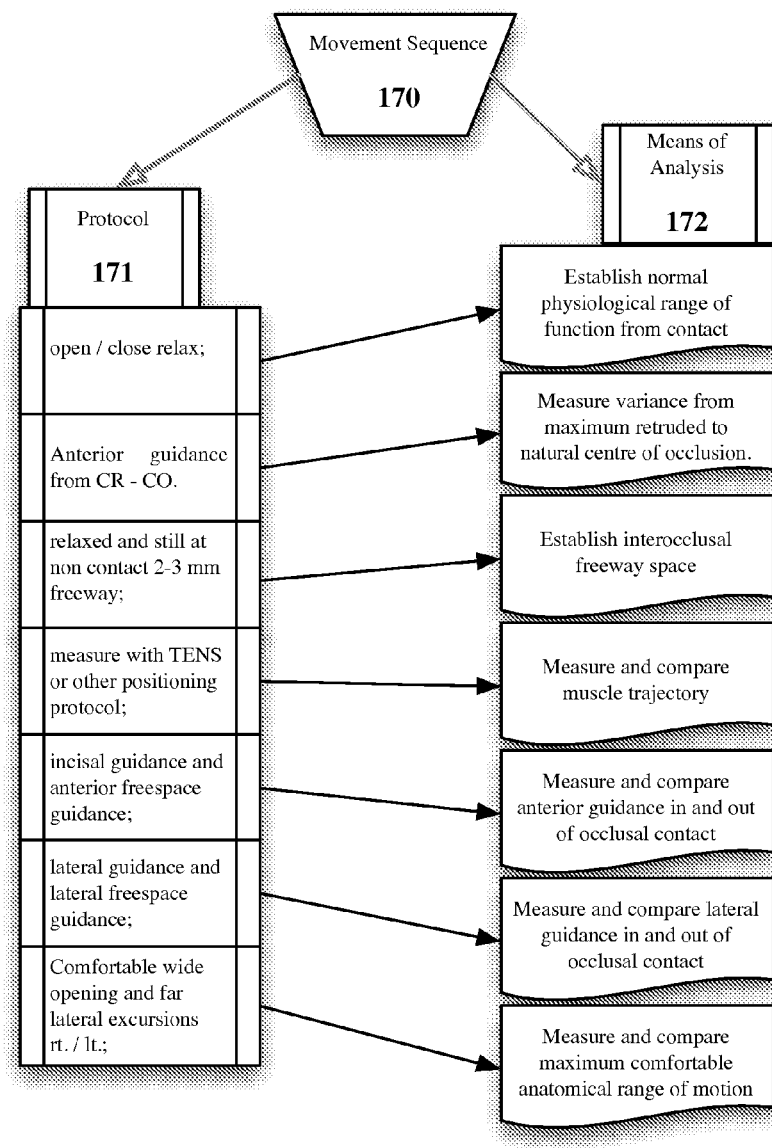

FIG. 17 Clinical process and documentation collection Architecture

Figure 18:
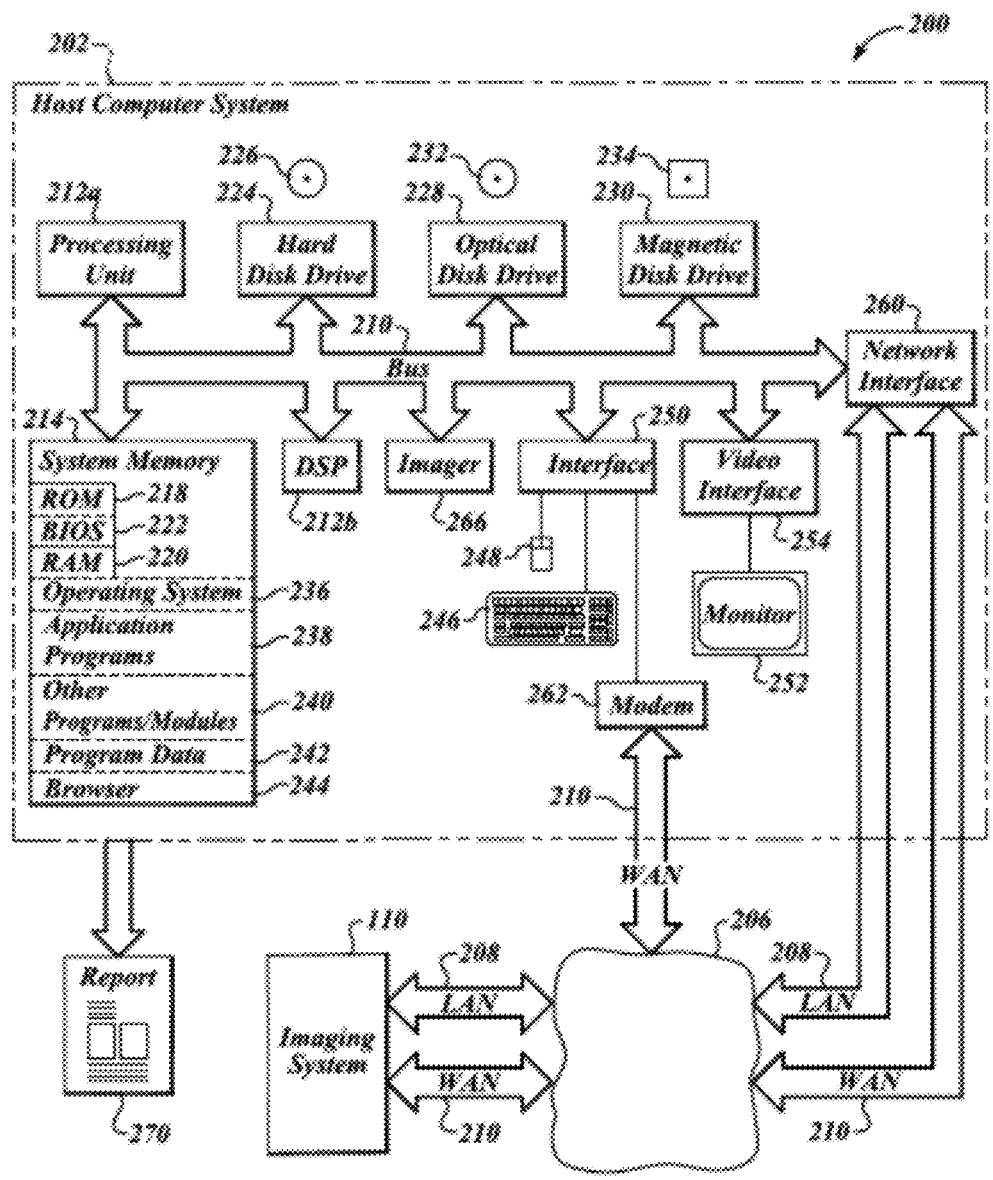

FIG. 18 is a schematic diagram of an imaging system and image processing host computing system, remotely located from and communicatively coupled to the movement imaging system, according to one illustrated embodiment.

DETAILED DESCRIPTION OF THE INVENTION

Definitions

The term "centric occlusion" is used to define the position of maximum intercuspation of the teeth, or other similar positions such as neuromuscular occlusion as would be known to one skilled in the art.

The term "biomechanical model" is used to describe a mathematical integration of data into a form where it can visualized and analysed.

Optical data or Image data is used to define the data acquired from a series of optical images where a 3D fiducial marker is tracked to measure the relative motion of the mandible from the maxilla Combined data is used to define the integration of Optical data with data from other sources such as accelerometer, gyroscope or radiology data.

As used herein, the term "about" refers to a +/−10% variation from the nominal value. It is to be understood that such a variation is always included in a given value provided herein, whether or not it is specifically referred to.

Unless defined otherwise, all technical and scientific terms used herein have the same meaning as commonly understood by one of ordinary skill in the art to which this invention belongs.

Figure 9:
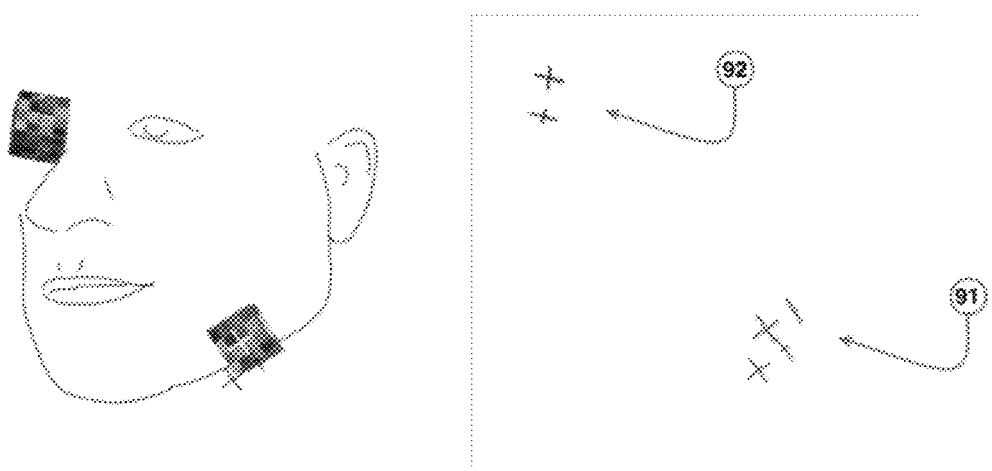
FIG. 9 illustrates Normalized Data from two different images and shows how mandibular tracking points can be extracted and measured from their normalized relative maxillary reference position.
Figure 10:
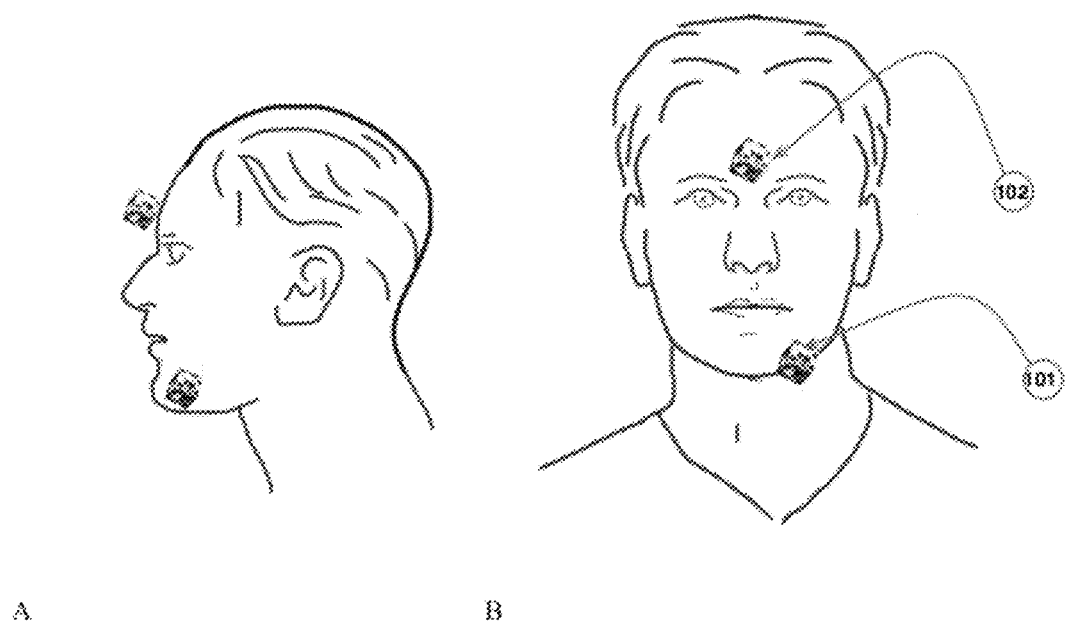
FIG. 10 illustrates Saggital (A.) and Frontal (B.) views of maxillary and mandibular optical target on a harness to capture X, Y, Z rotation and translation data.

The present invention provides a mandibular optical target 101, a cranial optical target 102, a means for capturing the data from an image or image sequence FIG. 9, and means for communication of such data 124, a mathematical model of the biomechanics of this data, and a means to display such data 163 and mathematical model that would enable one to make an analysis 164. Normalized data from two different images can be combined and the tracking points on the cranium aligned 92 and the variation in the image sequences can be computed or displayed 91.

One object of the invention is to provide a means of analysis 172 such that cranio-mandibular functions and structure can be easily correlated for treatment and data management.

Figure 11:
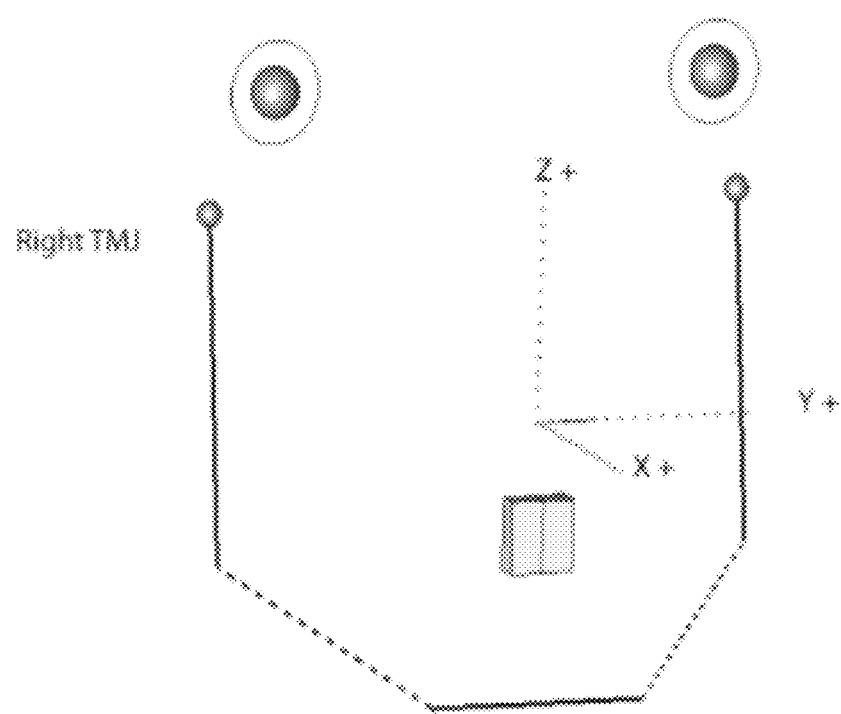
FIG. 11 illustrates how the orientation of planes is distinguished, as used in many medical imaging techniques. A X-Y-Z cartesian coordinate system with the X-axis going from front to back, the Y-axis going from left to right, and the Z-axis going from up to down. The X-axis axis is always forward and the right-hand rule applies.

Data is presented in a manner to include details of cranial, maxillary and mandibular relations, include rotations and vectors at around all the standard and accepted conventions such as positions of occlusion, freeway space, or temporomandibular joint functions and to characterise normal and pathological functions, FIG. 11. The associated analysis or analysis services could allow for knowledge to be shared between conventional dental laboratories and clinicians. Laboratory services can be inclusive of diagnostic reports and data management 165 and include date from third party laboratories.

One aspect of the invention is to create a method of measurement and reporting of inter-occlusal space including centric occlusion, that could be widely or globally accepted. In one embodiment of the invention, measurements are collected from various sources 132, are transmitted to an offsite analysis centre 133, and used in an analysis of the clinical data 135, including the data being compared to a biomechanical model for normalization and visualization 134, the integration of data to calculate forces and displacement, the integration of data into the biomechanical model 137, and the integration of data into an timeline analysis model 138. The invention may be used to compliment or even replace physical measurements and articulation of occlusion either by computer modeling or by mounting physical casts. In this regard another objective of the invention is to improve the communications with the laboratory without having a system that is cost prohibitive in the time required or be difficult to implement without substantial training.

It is one aspect of the invention to measure and use data in a biomechanical model that integrates the variations of the forces and or stressors that are induced upon tissue structures that may cause them to adapt by compression or stretching or long term morphologic changes. The motion of the mandible itself can be described as a rigid three dimensional body that can be measured within its constraints of free movement of its six degrees of freedom, in three dimensional space. However the relationship between the maxilla and the mandible is not fixed and its centers of rotation are not constant and it is useful to be able to measure such changes. The rotational axis of the mandible depends on the degree of soft tissue compression such as with the articular disk and the centers of effort for the many muscle and ligament origins and insertions. The slope of the articular eminence also has a significant impact on the actual movement. The condyle of the mandible may rotate and translate in the articular fossa to a varying degree depending upon the forces acting upon it. It can therefore be seen that the invention is a system and a method of clinical and laboratory practice where the architecture and function of the jaw and teeth can be measured and collected as digital image data.

Accordingly the invention could be used in comparing the form and function of not just the tooth occluding surfaces and temporomandibular joints, but also the entire crainio mandibular system including but not limited to bones, teeth, muscles, ligaments and nerves and further providing graphic representations of the changes that would not be obvious from manual methods of trying to determine the function from the structure, such as comparing opposing tooth surfaces. This is especially the case for dentists and doctors such as maxillofacial surgeons, ear nose and throat specialists, and laboratories and technicians providing prosthetic, tooth positioning and occlusal appliances. Three dimensional force and movement data with six degrees of freedom, of both maxillary and mandibular activity, can with the invention, be made available and can be compared to the structure, and function of the stomatognathic system. Clinical procedures 171, which require interpretation of functional data such as occlusion, will by this system, be able to document or record those functions 172.

Still yet further, another feature of the invention is to create a speed advantage over existing procedures. Rather than using mechanical methods to record a patients structure and function a protocol of patient scans can be enabled with the invention and this would enable the modeling of the movement and spatial frequency of the jaw and cranium in three dimensions.

Since the center of soft tissue rotation may not be the same as that as directed by the bony structures, then there is likely to be a varying level of soft tissue compression as the mandible is put under rotational or translational stress.

Figure 1:
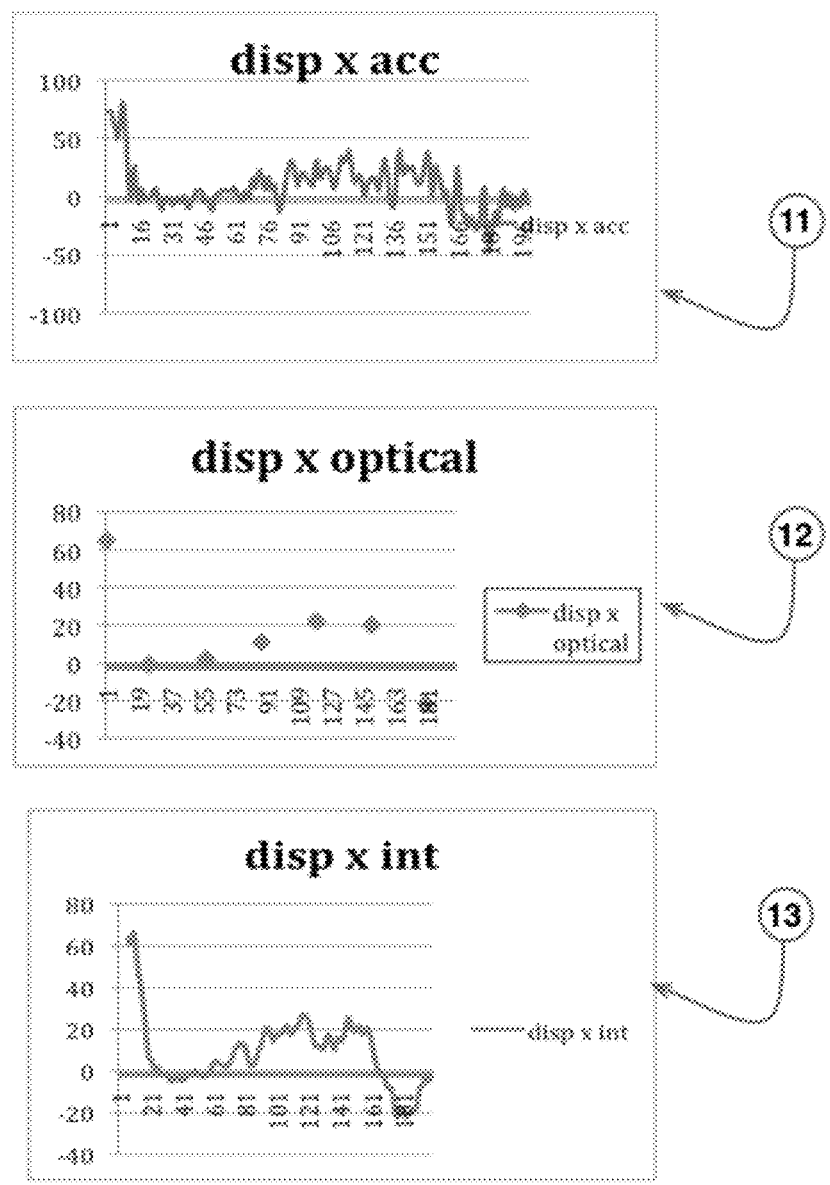
FIG. 1 illustrates y axis and z axis plots of high frequency data from an accelerometer data integrated to show displacement over time and low frequency data from optical imaging further integrated together where the optical data can spatially normalize it.

Since the actual position of the centre of force is not fixed, the invention can make calculations of the changes inherent on the mandible by measuring its rotations and translations during different functions FIG. 1. For instance the rotation and translation of the mandible is different in many people such as when they are under stress from physical exertion, especially as compared to talking, eating or other normal functions FIG. 3.

Figure 4:
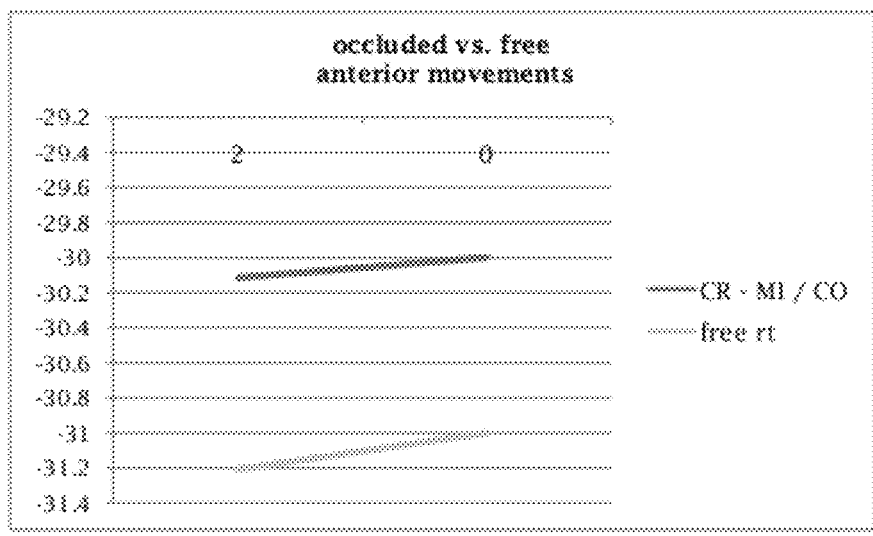
FIG. 4 illustrates Translation during occluded movement from the retruded position to CO is compared in relation to free space movement in the same direction based on dental and muscle/Temporomandibular joint guidance.
Figure 5:
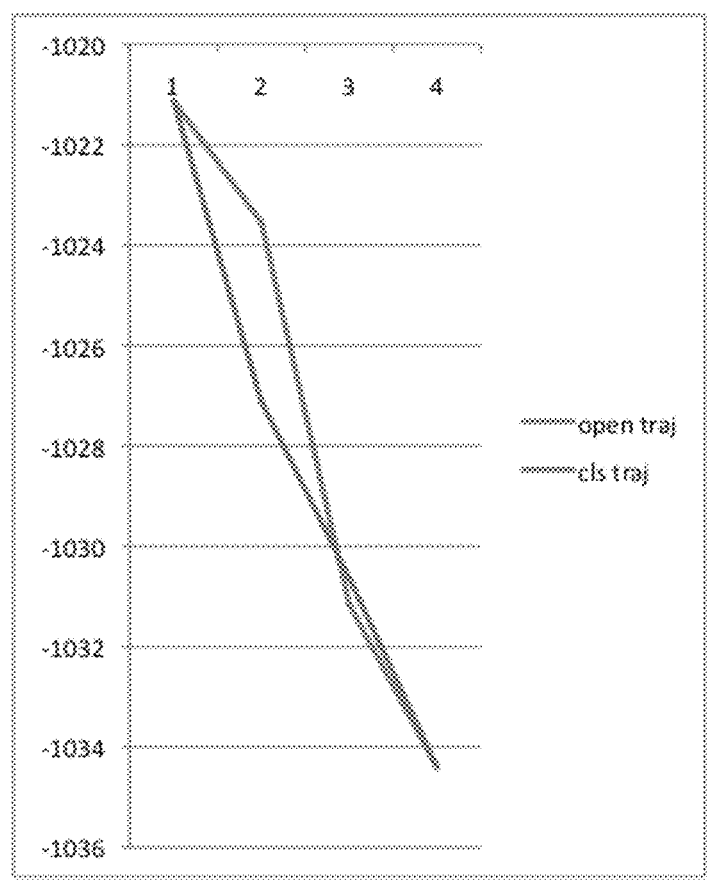
FIG. 5 illustrates opening with the effect of muscles causing retrusion as compared to closing where opening muscles have relaxed, from optical data.

In fact the measurement of the forces under exertion may create a completely different occlusal relationship, than that of what is considered as centric occlusion FIG. 4. Furthermore a forced occlusion may be in a position that if not balanced could be causing soft tissue stress or could be putting the masticatory nervous system under such stress that it could impact other systems in the body. As a result it is one objective of the system to be measuring the variations between normal and high strain rotations and translations.

In one embodiment the systems have three dimensional fiducial targets on a mandibular harness 101 and three dimensional fiducial targets in a maxillary harness 102. The targets are mounted such that their three dimensional structure can be visualized in frontal and sagittal views. This configuration and can be used to measure the changes in the plane of their rigid body in euclidian space. In turn the maxillary and mandibular relationships can also be determined. The use of two patterned three dimensional fiducial targets allows for the ability to measure, and subsequently visualise, with 6 degrees of freedom the absolute changes in acceleration, velocity and displacement of the mandible and also the maxilla and subsequently the relative movement including force vectors and rotations, of the mandible to the maxilla such as the plane of occlusion of the mandible to the plane of occlusion maxilla. The rotational components of any dental or mandibular structure can be described in terms of the rotational component of the target data vs. the translational component of the target data.

The optical data can be captured by a single video camera or by taking a series of still images of the subject in motion. Enhanced detail may also be useful by taking additional in motion or still images from different angles. The displacement of points on the mandibular fiducial marker can be tracked by motion tracking software, and their spatial coordinates input into a biomechanical model, with the reference data of the size and shape of the mandible and face being input as measurements from the image, either by image interpretation software or by measurement of anatomic or additional marking points to register such measurements as the length and width of the mandible, including the ramus, the position of the condyle, the incisal position and other data as may be known to one skilled in the art as necessary to complete a biomechanical model of the tempromandibular, maxillomandibular or craniomandibular relationships in various levels of detail. In one embodiment of the invention, a three dimensional fiducial target module is small enough that it can be used either intra-orally or extra-orally without cumbersome or bulky apparatus or fixation procedures which would interfere with the clinicians duties of assisting the patient while using the invention for recording the changes in physiology or kinematics.

In another embodiment the fiducial target is projected onto the moving surface such as a tooth, and the changes in surface translation with respect to the projected target can be measured. In one embodiment, the resolution of the imaging and data tracking may not allow for anything but low frequency data to be collected 12. This could be the case where the imaging of the patient is limited to two or three images with the jaw in excursive positions. However, this may be enough data for many applications, and can further be integrated with other data 13, such as accelerometer data 11, or prior model data to create a data file.

The system performs an analysis of the displacement at various positions so that the relative motion can be related to the various muscle and other soft tissue variations and compared as might be expected within the constraints of the maxillo-mandibular anatomy and physiology.

In a slightly different embodiment which is a simplified modification of the first example, the system has only a three dimensional fiducial target on the mandible. This may be all that is required in many situations especially if a second accelerometer or gyroscope is placed to provide corrective measurements of the Euler rotations around the vertical axis rotations. These are critical to measuring the rotations during cuspal alignment or tissue compression.

In one embodiment image data 150 is used with an accelerometer based tracking system 155 is used to refine the data. Other data, such as MRI, CT 154, Ultrasound and physical measurement data can also be used to increase the accuracy of the results. Their outputs can be incorporated by integration 152 using the various types of data using a Complementary Filter, Kalman Filter, or similar Filter. This is sometimes referred to as Sensor Fusion. The Complementary Filter uses two orientation estimates, with differing noise characteristics, to produce a single orientation estimate combining the advantages of each. Data filtering with fiducial target tracking can be utilized in this way to provide an estimate of the position and velocity of a target at the time of measurement.

The first three dimensional position is calculated from the initial image in a sequence. The second three dimensional position is calculated from a second image in a sequence and can be used as a first estimate calculated from a biomechanical model of the human jaw function and used to establish an estimate of the person specific movement patterns. Further images and positions can be calculated to improve the accuracy of the biomechanical model. The deviations from a standard biomechanical model can be used for diagnostic purposes. The biomechanical model as imaged for a patient at one time can be compared to biomechanical model created at another time and can also be used for diagnostic purposes. Such diagnostics with three dimensional range of motion with six degrees of freedom could include, orientation of the planes of mandible to maxilla, such as the occlusal plane, the rotation and translation of the temporomandibular joints and the impacts of muscle activity FIG. 14 on the biomechanical model.

The estimates of the biomechanical model can be used as inputs to the Complementary Filter, utilizing the best qualities of each individual data source to obtain a "fused" output of both data estimates 157. A series of images from the first used to describe the initial position such as an occlusal contact 32, to a position describing a known biomechanical relationship such as a neuromusculatory neutral position 33, can be used to match and predict the next position 34, and the variance can be noted in the differences between the expected and measured data, as a filter looking for functional deviations from normal.

The combined outputs of the filter provides a fusion of refined estimate of the position and range of three dimensional motion relative to a patients physical characteristics. Inputs of shape and size of the mandible and cranium can be input into the model as a means of customizing the model to the patient. Such inputs could include the size and shape of the mandible, the incisal position, the plane of occlusion and other known planes and anatomical points that would be known to one skilled in the art. This output can be further filtered to enhance or extract specific features of the biomechanical model. Such features may be things like the differences in high frequency data 11, and low frequency data 12, and its effect on TMJ position FIG. 2A, axis of rotation, and translation. In this case a matched filter is applied to the measured signals to extract the presence of such features at levels that would not normally be observable. Other filters such as simple lowpass, bandpass, and high pass filters are used to extract low frequency, high frequency, and specific frequency characteristics of the jaw dynamics as the jaw is exercised through a prescribed set of motions. These filters can be of the Finite Impulse Response or Infinite Impulse response if implemented digitally, or any of the many forms of analog filters.

In order to use either the low frequency data or combined data to characterize function, the images can be reported with time values, which would allow integration to characterize velocity or acceleration. This is well known and understood to those in the art. The image data can be used to calculate the rotations of the jaw and can be used in an integrated mathematical model of jaw biomechanics including analysis of the stressors on that might impact the physical motion FIG. 7.

Data Analysis

Figure 6:
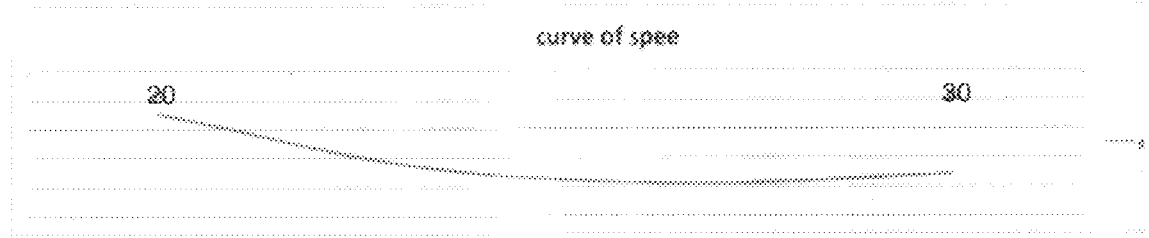
FIG. 6 illustrates an ideal curve of spee based on free space movement and Temporomandibular joint guidance from optical data.

This system may be used to measure the resistance in various muscle groups and correlate the resistance to diagnostic criteria such as the ideal design and three dimensional variations from an the curve of spee FIG. 6; the resistance vs. compression of the temporomandibular joint; the axes of compression on joint tissues; and on compression of dental occlusal and alveolar structures, including the axes of the forces involved in relation to the axial alignment of the teeth or prosthetics.

Such relationships can include mechanical computations of such things as inertia, resistance, repeatability, stress, positions and their co-relationships. In this model the system can reference three-dimensional movements of the jaw to the forces and characterise the relationship of the velocity and force such that one can reference the muscle activity as a function of movement FIG. 14.

The system can be used as a method of presenting standardised dental documentation and procedures FIG. 17, including protocols 171 and means of analysis 172. Analysis of the Temporomandibular Joint can be done in specific ways to represent a standard test to relate Temporomandibular Joint function to occlusal function. In other fields, document designers have long created sets of documents which all share a common structure. In this case the document created is a combination of prescription, protocol and analysis that can be created as part of a patient record, whether digital or otherwise, and which can incorporate digital simulation records.

A prescription or treatment plan, would involve choosing from a series of scans from a list in a protocol 171, including the following:
open/close relax;
relaxed and still at non contact 2-3 mm freeway;
measure with TENS or other positioning protocol;
incisal guidance and anterior freespace guidance;
lateral guidance and lateral freespace guidance;
Comfortable wide opening and far lateral excursions rt./lt.;
Anterior guidance from CR-CO.

Data Display

These protocols represent a standard analysis and a format of common structure for using optical fiducial tracking to collect data in a clinical setting. It also represents the style for which a set of documents for Temporomandibular Joint analysis and Occlusal analysis can be performed. These documents may be in the form of images or formats for a class of occlusion and Temporomandibular Joint analysis documents. This further simplifies the task of creating and interpreting multiple scans by providing a predefined set of options within which to work.

Figure 7:
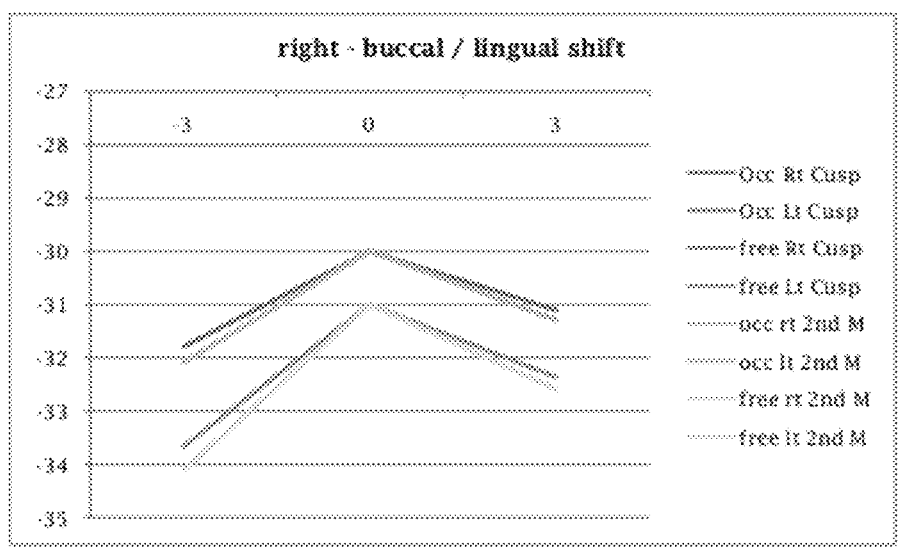
FIG. 7 illustrates right side translations based on free space movement and temporomandibular joint guidance from optical data. Right buccal cusps suggest superior and retruded position of temporomandibular joint and masseter involvement.
Figure 8:
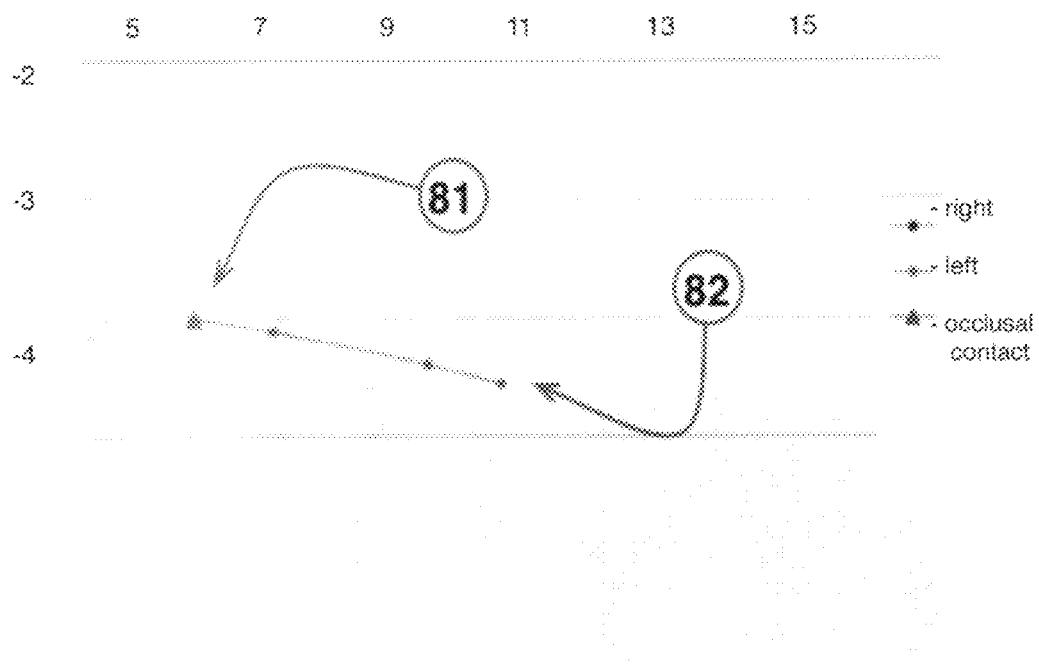
FIG. 8 illustrates the position of the tooth contacts in relation to the right and left TMJ displacement plots, from accelerometer integrated with optical data. In this case CO is in the Gelb 4/7 position, the original TM locus, and shows translation from there.

In one embodiment the system provides an analysis that can be used as a document graphic or multi dimensional computer graphic representation, of the biomechanical model data compared to relative positions of anatomical structures or the relationship between anatomical structures. The biomechanical model can be further enhanced with data to demonstrate the changes in both velocity and displacement. FIG. 7 shows acceleration data overlay for the internal slopes of the cusp of a posterior 2nd molar vs. that of the cuspid guidance.

A Biomechanical Model

The biomechanical model of the jaw can be used and customised for each patient. This model is analogous to a fully adjustable dental articulator, however, able to compensate for soft tissue variations in a way that no other model might be able to do as it incorporates the contractile and elastic components in each type of tissue. This model will be useful for either the clinician or support personnel including laboratory personnel. The biomechanical model can be used for instantaneous evaluation or compared to a time series.

Accordingly the biomechanical model incorporates physical measurements with respect to the angle of the jaw, the ramus, the condyle, the width between the condyles in the frontal plane and other details as would be necessary to describe the anatomy. Such measurements could be patient specific or based on standardised normals or some combination thereof. In the case of the invention the model can relate the forces from muscle activity as can be interpreted based on changes in displacement as the jaw functions. These can in turn be used to correlate to such conventions as centric occlusion, or bennett shift and other well known terms that relate to function, but with the added data to compare ideal form to actual form and to compare forces versus actions.

In one embodiment the biomechanical model is used in a process of treatment 161, whereby the model can be updated 162 based on the movement sequence 170. The data is transmitted to the central lab or host 167 and is processed and further sent to the doctor 163, who is enabled to review by the documentation process 139 and display 168. In making an interpretation of the data, the data can be further made available to the host laboratory in order to update the patient file.

Measurement of Lateral Function

In one embodiment the invention can use its biomechanical model for the comparison of lateral functions of the jaw with the teeth in occluded contact vs. the lateral functions of the jaw without any contact of the dentition. In this case the patient moves the jaw laterally from CO while maintaining occlusal contact. Similarly the patient moves the jaw laterally from a relaxed position with some freeway space from CO. FIG. 7 shows the difference between occluded and non occluded movement.

Measurement of Muscle Interferences on Displacement Data

The position of the jaw tracking versus the muscles and ligaments involved in the biomechanical model by comparing the acceleration and deceleration as would be expected with muscle activity and the expected resistance that would be part of a standardised model or with respect to prior data from a subject.

A normalised database that provides reference data of the contractile and elastic components in each type of tissue that would control the jaw function. Changes in acceleration can be referenced with a biomechanical model related to different type of functions. For instance, the movement of opening and closing the jaw uses the components of movement differently from the movement of anterior translation while in occlusion.

The system provides an analysis that can be used to describe the function of the muscle movements compared to combined image data, based on the measured or statistical anatomical relationships of the cranio-facial muscles. A biomechanical model of the maxillo-mandibular function can be manipulated by the input of the data. Such a model might for instance, infer the actions of hyoid muscles vs. pterygoid muscles.

The form of the dentition might further be associated with the posture of the jaw and the posture of other parts of the body such as cervical spine and anterior head posture. Such relationships might involve adding manually or by other sensors or imaging tools 132, measured variables of the spine or other body structures into the analysis.

Measurement of Forces, Including Angular Guidance on Tooth Positions

Figure 3:
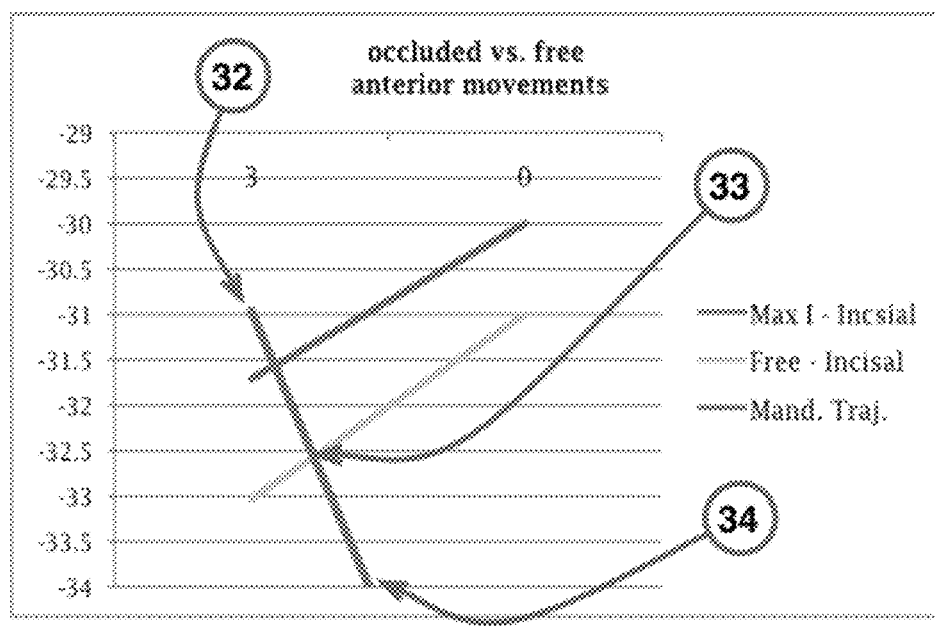
FIG. 3 illustrates incisal guidance and free translation without contact. The average direction of mandibular forces is shown orthogonally to the translations. The difference between muscle and tooth related guidance can be visualized.

The motion of the jaw has impacts upon the teeth as they come into contact FIG. 3, and contact points and the axial inclinations of the teeth can be compared including the ideal relationships to compare the vectors of the forces of occlusion in comparison to the actual or proposed positions of teeth.

Measurement of Forces on Temporomandibular Joint Positions

A position of the condyle in the glenoid fossa can be seen as the locus of a point of the superior surface in contact with the articular disk 81. The temporomandibular joint can be compared when measured both with and without stress, including measurements made when in a relaxed static posture vs. that of a clenched posture or anterior translation resulting from lateral movement of the jaw. The muscle involvement can be compared with the normal vectors compared to those at stress vectors. Other features of temporomandibular joint position can be evaluated and determined including:

articular disk position can be calculated from the presence or absence of abrupt changes as compared to the normal or to a time series;

the centre or resistance and total joint resistance and compression can be calculated from the variations in movement during diagnostic scans and also from changes as compared to the normal or to a time series;

joint laxity can be calculated by comparative scans that show lack of repeatability in translational position or changes as compared to the normal or to a time series, especially in the changes in high frequency data;

clicks and crepitus can be calculated by comparative scans that show the variations in high and low frequency data or changes as compared to the normal or to a time series. A computed model of temporomandibular joint biomechanical function can then be created that integrates all the data and can be visualised and compared over time.

Deriving Ideal Form from Function.

In one embodiment of the invention, the ideal shape and relationship of the maxillary dentition in comparison to the anatomical structures of the mandible and its functional components such that an ideal Curve of Spee FIG. 6. can be calculated and or displayed as a complex curve or three dimensional shape or four dimensional analysis such as compared to the actual curve of spee or compared to a timeline. The timeline might be a forward looking projection based on how the muscles and stressors might cause hard and soft tissue changes over a variable age of a subject.

The greater proportion of dental treatments can be completed using this method with reasonable knowledge of the position of the temporomandibular joints and their actions. The measurements are easily made and easily become part of standard treatment protocols such as would be incorporated into routine clinical practice with analysis of the patients centric occlusal and centric relation zones and other such anatomical relationships well documented to a standard protocol.

Treatment Methods

Laboratory Method of Describing and or Machining of a Custom Articulator Insert.

In one embodiment of the invention, the data can be used to produce a list of the settings to allow laboratory technicians to manually adjust physical or virtual articulators, such setting based on the image data or combined data alone or in conjunction with clinical measurements. In articulators that can accommodate inserts for condylar guidance or for incisal guidance, then these inserts could be automatically machined from the image data or combined data. In virtual articulators the image data or combined data could be used to program similar functions as would be known to one skilled in the art. Likewise, occlusal paths such as the idealised curve of spee, could be machined to allow clinicians and technicians to understand and manage the anterior and posterior three dimensional space of a subject's occlusion. In the case where an analysis is being made or a prosthesis is being designed on a computer, the system can provide reference data that would be used for programming an adjustable, digital or virtual maxillo mandibular relationship.

Data that is measured with the state of the art for analysis of dental features can include diagnostic solutions such as radiographs including peri-apical and panoramic or cephalometric images, manual anatomical measurements, such as jaw size, video and photographic images, simulations, intra oral force measurements, kinesiographs, face bow tracings, three dimensional scans of the actual dentition or of impressions or casts made from the actual dentition or scanning data from MRI or CAT scan data comparing function or state of the temporomandibular joint. Any or all of these diagnostic solutions 132, can be combined with the image data or combined data and used for further diagnosis 135, or combined to be used in a computer based presentation that allows multiple parties to receive reports 139, view the information over the interne.

Mechanical and Electrical Considerations

The fiducial target may to be mounted to the jaw, head or teeth by means of temporary cement, a means of a harness, clamp and or straps, or with a bite fork system that can be used with any of the standard methods of incorporation of a relationship with a dental articulator or other methods of jaw measurement as would be widely know in the art of dental practice.

In one embodiment the image capture side of the invention consists of a camera connected to a single board computer, or camera with on board processing, where all data storage is kept in a location offsite in a database with reports and analysis being handled by an offsite lab service as shown in the High Level system architecture FIG. 12:

A micro-controller board (a single board computer) that runs a multi-tasking operating system kernel, industry standard networking software and some custom-written software modules that a) capture data from the Imaging Module and b) submit that data to an Internet-based server for post-processing and analysis.

The imaging camera can be triggered by operational module micro-controller capture software, which can keep a time stamp to calibrate the image data with the accelerometer data or other sensors or imaging tools, before and during data capture. Once the capture window ends the capture software can assign the data a timestamp and other pertinent information in a file.

The micro-controller reporting software then picks up any files that are ready on a regular basis and submits them, across the Internet, to the dental analyzer server. The mechanism allows for file retries and storage until a network connection becomes viable.

The image processing host computer system 202 may include a hard disk drive 224 for reading from and writing to a hard disk 226, an optical disk drive 228 for reading from and writing to removable optical disks 232, and/or a magnetic disk drive 230 for reading from and writing to magnetic disks 234. The optical disk 232 can be a CD-ROM, while the magnetic disk 234 can be a magnetic floppy disk or diskette. The hard disk drive 224, optical disk drive 228 and magnetic disk drive 230 may communicate with the processing unit 212 via the system bus 216. The hard disk drive 224, optical disk drive 228 and magnetic disk drive 230 may include interfaces or controllers (not shown) coupled between such drives and the system bus 216, as is known by those skilled in the relevant art. The drives 224, 228 and 230, and their associated computer-readable storage media 226, 232, 234, may provide non-volatile and non-transitory storage of computer readable instructions, data structures, program modules and other data for the image processing host computer system 202. Although the depicted image processing host computer system 202 is illustrated employing a hard disk 224, optical disk 228 and magnetic disk 230, those skilled in the relevant art will appreciate that other types of computer-readable storage media that can store data accessible by a computer may be employed, such as magnetic cassettes, flash memory, digital video disks ("DVD"), Bernoulli cartridges, RAMs, ROMs, smart cards, etc.

Program modules can be stored in the system memory 214, such as an operating system 236, one or more application programs 238, other programs or modules 240 and program data 242. Application programs 238 may include instructions that cause the processor(s) 212 to automatically normalize digital images or information therefrom based on fiducial markers in those digital images and/or compare or lesions between normalized digital images. Other program modules 240 may include instructions for handling security such as password or other access protection and communications encryption. The system memory 214 may also include communications programs for example a Web client or browser 244 for permitting the image processing host computer system 202 to access and exchange data with sources such as Web sites of the Internet, corporate intranets, extranets, or other networks as described below, as well as other server applications on server computing systems such as those discussed further herein. The browser 244 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document. A number of Web clients or browsers are commercially available such as those from Mozilla, Google and Microsoft of Redmond, Wash. While shown in FIG. 18 as being stored in the system memory 214, the operating system 236, application programs 238, other programs/modules 240, program data 242 and browser 244 can be stored on the hard disk 226 of the hard disk drive 224, the optical disk 232 of the optical disk drive 228 and/or the magnetic disk 234 of the magnetic disk drive 230.

An operator can enter commands and information into the image processing host computer system 202 through input devices such as a touch screen or keyboard 246 and/or a pointing device such as a mouse 248, and/or via a graphical user interface. Other input devices can include a microphone, joystick, game pad, tablet, scanner, etc. These and other input devices are connected to one or more of the processing units 212 through an interface 250 such as a serial port interface that couples to the system bus 216, although other interfaces such as a parallel port, a game port or a wireless interface or a universal serial bus ("USB") can be used. A monitor 252 or other display device is coupled to the system bus 216 via a video interface 254, such as a video adapter. The host computer system image processing can include other output devices, such as speakers, printers, etc.

The image processing host computer system 202 can operate in a networked environment using logical connections to one or more remote computers and/or devices. For example, the image processing host computer system 202 can operate in a networked environment using logical connections to one or more network server computer systems (not shown). Communications may be via a wired and/or wireless network architecture, for instance wired and wireless enterprise-wide computer networks, intranets, extranets, and the Internet. Other embodiments may include other types of communication networks including telecommunications networks, cellular networks, paging networks, and other mobile networks.

The server side of the dental analyzer consists of: Industry standard web server software with custom-written scripts for submitting received data files from the imaging system into the dental analyzer database; Industry standard web server software with custom-written scripts for submitting received data files from the dental imaging system into the dental analyzer database; database server software with custom-designed table structures for accommodating the dental analyzer capture data sets.

In one embodiment the server could be localized with the clinical capture side.

The data from all axes including rotations may be used with other circuitry and systems as would be normal for one skilled in the art of electronics design.

Signal Processing Method for Noise, Artifacts, and Missing Data

The image data or combined data 157, can be filtered to be sensitive to the frequency of movements to be measured. For instance, the broad movements of opening and closing show a different frequency distribution than the vibration of the jaw in a static position. By describing the low vs. the high frequency data relative to the displacement of the jaw the signal processing system can reduce the noise in the data, and also point to patterns that might be useful in determining the normal functions, or pathophysiology.

Noise and Artifact Sources

The image data 150 or combined data 157 is also filtered to remove noise and interfering signals. The image data or combined data can be contaminated by noise and artifacts that can be within the frequency band of interest and can manifest with similar morphologies such as with accelerometer data 155 by itself. Broadly speaking, noise contaminants can be classified as:

Power line interference, especially in areas with substantial medical equipment; Baseline calibration and drift; sensor pop or contact noise: Loss of secure contact between the fiducial marker and the patient and the skin manifesting as sharp changes for periods of around 0.1 second; Patient-System motion artifacts: Movement or imbalance of the fiducial marker system away from the contact area on the skin or teeth, usually manifesting themselves as rapid (but continuous) baseline jumps for up to 0.5 second; Data collecting device noise: Artifacts generated by the signal processing hardware, such as signal saturation; Electrosurgical noise: Noise generated by other medical equipment present in the patient care environment at frequencies between 100 kHz and 1 MHz, lasting for approximately 1 and 10 seconds; Quantization noise and aliasing; Signal processing artifacts (e.g., Gibbs oscillations).

Although each of these contaminants can be reduced by judicious use of hardware and experimental setup, it is impossible to remove all contaminants. Therefore, it is important to quantify the nature of the noise in a particular data set and choose an appropriate algorithm suited to the contaminants as well as the intended application as would be well known to one familiar with the art.

The invention will now be described with reference to specific examples. It will be understood that the following examples are intended to describe embodiments of the invention and are not intended to limit the invention in any way.

EXAMPLES

Example 1

One example of the invention is to be able to compare the form of the physical dental and jaw structures to their function. Where a single position of analysis might have previously been limited to one location, such as the probable position of CO, a functional analysis could enable the ability to look at occlusion as a comparison of forces and zones of interaction. So rather than provide clinical or laboratory personnel who are tasked to enable changes to a restoration or appliance with extremely limited information, less than what is ideally required to a complete their task, the invention provides clinicians and technicians detailed data regarding the rotations and translations of the relative maxillary and mandibular relationships.

Example 2

In another example of the use of the system, data can also be related to methods used normally such as recording the structure with impressions of the teeth and the subsequent articulation of casts with mechanical bite registrations. In this way the invention can use automated records of occlusion compared to such information that might be obvious from examining the wear facets on the casts such as group function of the teeth. The invention can be used to relate multiple versions of occlusal registrations that would be used to relate articulated casts in their static position to function, either intuitively by the clinician or technician, or to adjust a computer model or adjustable articulator. The invention would provide further information as might not normally be available such as tissue compression in the temporomandibular joint, or axial stress upon the teeth or from alveolar arch tissue under a prosthesis or surrounding an implant. In the case of an implant, a most important issue is to determine the relationship of axial forces of occlusion vs. the angle of the implant. This critical information will help technicians to build restorations with considerably less risk of failure.

Example 3 in another example of the use of the system, the invention is a analysis system and method to characterise the relationship between structure and function providing a solution for routine clinical analysis of Centric Occlusion, Centric Relation and axial forces, translations and rotations such that the information and data is easily correlated or visualised in two or three dimensions in comparison to any other point in the occlusion or temporomandibular joint. The movement data that relates to the position of the mandible in relation to the maxilla can be used to interpret the rotational and translational loading on the temporomandibular joint. The muscle bearing loads can be established and their impacts on the centre of effort or centre of rotation can be calculated. The rotations and translations of the condyle can be simulated as can the forces impacting the surrounding tissues.

Example 4

In another example of the use of the system, the fiducial marker shapes are configured to be the largest size that is reasonable for the depth of field allowing less image resolution or increased sensitivity/resolution, in order to reduce the impacts of vibrational noise from the optical imaging system to the resultant data. An intraoral imaging system would have a smaller depth of field and a smaller fiducial marker than an extra oral system.

Example 5

In another example of the use of the system, the mandibular fiducial marker shapes are clamped to the jaw using an apparatus that holds the markers in place inferiorly and posteriorly to the depressor muscles at the lower edge of the mandible near the insertion of the platysma. This enables the markers to be clamped to the patient with minimal interference. There are numerous cameras that are suitable for a low cost imaging system. Since the purpose of a lowest cost data capture is to measure the patterns of movement and compare to a biomechanical model, there is less demand for high frame rate and high resolution than might otherwise be required if the optical capture methods were used for high accuracy. If the fiducial markers are clamped to the mandible and cranium soft tissue, the data cannot be expected to be more accurate than the displacement that can occur due to muscle movements next to the clamp attachment points. However, by integration with a model or with other patient data, the low frequency data can be used to create a more accurate reproduction of the functions than could be expected with the data by itself.

It is obvious that the foregoing embodiments of the invention are examples and can be varied in many ways. Such present or future variations are not to be regarded as a departure from the spirit and scope of the invention, and all such modifications as would be obvious to one skilled in the art are intended to be included within the scope of the following claims.

I claim:

1. A method of operating a system for use in mandibular motion tracking, the method comprising: comparing by at least one processor an appearance of at least one shape of at least a first fiducial marker in a first digital image of the mandible to at least one defined actual shape of the fiducial marker; and an appearance of at least one shape of at least the same fiducial marker in a second digital image of the mandible to at least the first fiducial marker and at least one of correlating, normalizing, or correcting the at least the first digital image, based at least in part on the comparisons to subsequent images, and comparisons to the actual fiducial marker, including three dimensional comparison such that the rotations and translations of the mandible versus the maxilla can be measured as changes from the first digital image; said method further comprising a second fiducial marker mounted to the cranium in a manner whereby it does not move as a result of mandibular movement, said second fiducial marker being used for normalization or geometric correlation of the image data in a series of images.

2. The method of claim 1, further comprising: storing to at least one nontransitory storage medium the digital image as a multi-layer image file, or video file including a first digital image layer that stores and at least a second digital image layer that stores image metadata.

3. The method of claim 2, further comprising: registering a number of subsequent digital images in spatial and optical relationship by the at least one processor; and comparing the first and the subsequent digital images on a layer by layer basis by the at least one processor.

4. The method of claim 1, further comprising: establishing a subject specific baseline by the at least one processor which is specific to an individual; and wherein the normalizing is based at least in part on the subject specific baseline the first digital image and a plurality of sequential digital images, the sequential digital images sequentially captured at various times following a capture of the first digital image.

5. The method of claim 4, wherein determining a number of differences includes determining any morphological changes of the region of interest as the region of interest appears between the digital images as part of the determination of the differences in the region of interest as the region of interest appears between the normalized digital images including the first digital image and the plurality of sequential digital images.

6. The method of claim 1, further comprising: determining a number of patterns of movement between the normalized digital images including the first digital image and the plurality of sequential digital images, by the at least one processor, as part of a measurement of at least one of: rotation or translation or planar differences in jaw motion.

7. The method of claim 6, wherein determining a number of differences includes assessing any change in at least one structure of the temporomandibular joint, or the dental surfaces or occlusion, including rotations or translations or displacement of the jaw.

8. The method in claim 6, where the integrated data is used as a motion analysis for measuring the absolute changes and relative function of one anatomical structure to another. where the components of hard and soft tissue are used in analysis and where the deviations of the variables can be compared in a time series including velocity and displacement, such that the optical data can be correlated to probabilities of the involvement of various tissues of the mandible and or the maxilla in three dimensional space.

9. The method of claim 6, wherein determining a number of differences includes assessing at least one of the muscle forces of the stomatognathic system.

10. The method of claim 1, wherein normalizing includes normalizing at least the first digital image based at least in part on a biomechanical model.

11. The method of claim 10, further comprising: associating image timeline data to the digital model that geometrically represents the region of interest in three dimensions by the at least one processor.

12. The method of claim 10, further comprising: rectifying the tissue by the at least one processor with a three dimensional map of at least a portion of a the craniomandibular region which combines a set of three dimensional model probabilities with a correlation of a set of coordinate locations, and a set of complex interactions.

13. The method of claim 12, wherein generating a probability distribution of a motion being abnormal includes generating the probability distribution of the motion being abnormal based at least in part on a comparison of an frequency distribution that is attributable to temporomandibular disorder, including at least one of high or low frequency muscle forces, bilateral or unilateral positions or translations or rotations of the condyle, or degeneration of the condyle.

14. The method of claim 12, wherein generating a probability distribution of a motion being abnormal includes generating the probability distribution of the motion being abnormal based at least in part on a comparison of an frequency distribution that is attributable to dental occlusal changes, including at least one of high or low frequency muscle forces, bilateral or unilateral positions or translations or rotations of the teeth or changes in the tooth surfaces.

15. The method of claim 1, further comprising: generating a probability index by the at least one processor based on a combination of distributed properties of a number of variables including a normalization, a geometric correlation, comparison of high to low frequency data, a signal to noise characterization, or a defined diagnostic protocol.

16. The method of claim 1, wherein the instructions further cause the at least one processor to generate a digital model that geometrically represents the region of interest in three dimensions based on spatial data from the digital images.

17. The method of claim 1, further comprising: registering each of a plurality of digital images of the mandibular region by the at least one processor, including the first digital image, based at least in part on a variation between image layer coordinates in a temporal sequence of a plurality of digital images of the mandibular region.

18. The method of claim 1, further comprising: generating by the at least one processor a probability distribution of a motion being abnormal.

19. The method of claim 1, wherein a probability distribution of a movement being abnormal includes generating the frequency distribution with a probability index that weights at least some digital images according to at least one of a diagnostic value or a comparative amount of change between normal or anticipated movements and actual movements, such that displacements can be correlated to abnormal forces and positions of the temporomandibular joint or dental occlusion.

20. A system for use in jaw plane tracking, the system comprising: at least one processor; and at least one nontransitory storage medium that stores processor executable instructions which when executed cause the at least one processor to: compare an appearance of at least one shape of at least a first fiducial marker in a first digital image of a portion of a movement sequence to at least one defined actual shape of the fiducial marker; compare an appearance of each of a plurality of sections of the fiducial marker in the first digital image to respective ones of defined features of the fiducial marker; and at least one of correlate, normalize, or correct at least the first digital image, based at least in part on the comparisons; said system further comprising a second fiducial marker mounted to the cranium in a manner whereby it does not move as a result of mandibular movement, said second fiducial marker being used for normalization or geometric correlation of the image data in a series of images.

21. The system of claim 20, wherein the instructions further cause the at least one processor to store the digital image as a multi-layer image file, including a first digital image layer that stores and at least a second digital image layer that stores image metadata.

22. The system of claim 20, wherein the instructions further cause the at least one processor to store to a diagnostic layer of the digital image information indicative of at least one of dental occlusal changes, including at least one of high or low frequency muscle forces, bilateral or unilateral positions or translations or rotations of the teeth or changes in the tooth surfaces, or temporomandibular disorder, including at least one of high or low frequency muscle forces, bilateral or unilateral positions or translations or rotations of the condyle, or degeneration of the condyle.

23. The system of claim 22, wherein the instructions further cause the at least one processor to determine differences in the region of interest as the region of interest appears between the normalized digital images including the first digital image and the plurality of sequential digital images as part of a analysis.

24. The system of claim 22, wherein the instructions further cause the at least one processor to determine morphological changes of the region of interest as the region of interest appears between the digital images as part of the determination of the differences in the region of interest as the region of interest appears between the normalized digital images including the first digital image and the plurality of sequential digital images.

25. The system of claim 20, wherein the instructions further cause the at least one processor to register a number of subsequent digital images in spatial and optical relationship and to compare the first and the subsequent digital images on a layer by layer basis.

26. The system of claim 20, wherein the instructions further cause the at least one processor to establish a subject specific baseline which is specific to an individual, and normalize based at least in part on the subject specific baseline the first digital image and a plurality of sequential digital images, the sequential digital images sequentially captured at various times following a capture of the first digital image.

27. The system of claim 20, wherein the instructions cause the at least one processor to determine the number of differences by assessing any change in at least one of the temporomandibular movement, muscular forces or occlusal function.

28. The system of claim 27, wherein the instructions further cause the at least one processor to rectify the tissue with a three dimensional map of at least a portion of a body which combines a set of three dimensional model probabilities with a correlation of a set of coordinate locations, a set of spectral effects and a set of complex interactions.

29. The system of claim 20, wherein the instructions further cause the at least one processor to generate a probability index based on a combination of distributed properties of a number of variables including a normalization, an exposure correction, a geometric correlation, a signal to noise characterization, or a defined diagnostic protocol.

30. The system of claim 20, wherein the instructions further cause the at least one processor to generate a digital model that geometrically represents the region of interest in three dimensions based on spatial and movement frequency data from the digital images.

31. The system of claim 20, wherein the instructions further cause the at least one processor to perform a registration on each of a plurality of digital images of the tissue, including the first digital image, based at least in part on a variation between image layer coordinates in a temporal sequence of a plurality of digital images of the mandibular region.

32. The system of claim 31, wherein the instructions further cause the at least one processor to generate the probability distribution of the tissue being abnormal based at least in part on a comparison of a frequency distribution of movement data that is attributable to clicks or crepitus in the temporomandibular joint.

33. The system of claim 20, wherein the instructions further cause the at least one processor to generate an analysis comparison of layers in at least the first digital image as a histogram.

34. The system of claim 20, wherein the instructions further cause the at least one processor to generate a probability distribution of a tissue being abnormal.

35. The fiducial marker of claim 34, wherein the colors in the contrasting sections include at least one of black or white.

36. The fiducial marker of claim 34, wherein the colors in the contrasting sections include a plurality of different shades of grey.

37. The fiducial marker of claim 34, wherein the defined profile is a polygon.

38. The fiducial marker of claim 34, wherein at least one light source operable to project a virtual fiducial marker at least proximate the region of interest on the portion of the bodily tissue to be imaged, the virtual fiducial marker having a defined profile and a plurality of defined shapes; and an image capture device having a field of view and configured to capture digital images of the cranium including the region of interest, all encompassed by the field of view of the image capture device.

39. The imaging system of claim 34, wherein the virtual fiducial marker is projected with the plurality of defined shapes as straight line segments.

40. The imaging system of claim 34, wherein the virtual fiducial marker is projected with the profile of a circle and with the plurality of defined shapes as straight line segments emanating from a center point of the circular profile.

41. The system of claim 20, wherein the at least one processor follows a reporting protocol that includes one of: a therapy recommendation in the report based on the assessment, two or three dimensional display of the normal or pathophysiological states of the subject.

* * * * *